(12) United States Patent
Storozhuk

(10) Patent No.: US 12,100,142 B2
(45) Date of Patent: Sep. 24, 2024

(54) SYSTEM AND METHOD OF EVALUATING FLUID AND AIR FLOW

(71) Applicant: Materialise NV, Leuven (BE)

(72) Inventor: Oleksandr Storozhuk, Leuven (BE)

(73) Assignee: Materialise NV, Leuven (BE)

( * ) Notice: Subject to any disclaimer, the term of this patent is extended or adjusted under 35 U.S.C. 154(b) by 371 days.

(21) Appl. No.: 17/655,542

(22) Filed: Mar. 18, 2022

(65) Prior Publication Data

US 2022/0318994 A1 Oct. 6, 2022

Related U.S. Application Data

(63) Continuation of application No. PCT/US2020/052567, filed on Sep. 24, 2020.

(60) Provisional application No. 62/905,814, filed on Sep. 25, 2019.

(51) Int. Cl.
*G06T 7/00* (2017.01)
*A61B 34/10* (2016.01)

(52) U.S. Cl.
CPC .. *G06T 7/0012* (2013.01); *G06T 2207/30104* (2013.01)

(58) Field of Classification Search
CPC ......... G06T 7/0012; G06T 2207/30104; G06T 2207/20096; G06T 2207/20104; G06T 2207/10072; G06T 2207/30048; G06T 2207/30052; G06T 2207/30061; G06T 2207/30172; G06T 7/62; A61B 2034/104; A61B 6/469; A61B 6/504; A61B 6/507; A61F 2/24
See application file for complete search history.

(56) References Cited

U.S. PATENT DOCUMENTS

| | | | | |
|---|---|---|---|---|
| 2004/0154578 A1* | 8/2004 | Weaver | ................... | F01M 11/02 74/579 E |
| 2005/0131284 A1* | 6/2005 | Grinvald | .............. | A61B 3/1241 600/323 |
| 2006/0292972 A1* | 12/2006 | Ketels | ................... | A22C 25/142 452/179 |
| 2008/0021331 A1* | 1/2008 | Grinvald | ............ | A61B 5/14555 600/476 |
| 2010/0051248 A1* | 3/2010 | Inatomi | ................. | F28D 9/0037 165/166 |
| 2012/0155723 A1* | 6/2012 | Deno | ........................ | G06T 7/74 382/128 |
| 2013/0112794 A1* | 5/2013 | Castillo | .................. | B65H 57/14 242/147 M |
| 2014/0319035 A1* | 10/2014 | Burbank | ............. | A61M 1/1692 73/40.5 R |
| 2017/0220760 A1 | 8/2017 | Fonte | | |

(Continued)

*Primary Examiner* — Dominic E Rego

(74) *Attorney, Agent, or Firm* — Dinsmore & Shohl LLP

(57) ABSTRACT

Systems and methods of fluid or air passageway cross-sectional area determination in an anatomy are disclosed. In some examples, the methods may include generating a model of a structure based on a plurality of images of the structure, the structure comprising at least one fluid or air flow path. In some examples, the methods may also include identifying an obstruction element in the model of the structure, the obstruction element affecting the at least one fluid or air flow path in the model. In some examples, the methods may also include determining a region of the at least one fluid or air flow path for flow analysis.

20 Claims, 13 Drawing Sheets

(56) References Cited

U.S. PATENT DOCUMENTS

| | | |
|---|---|---|
| 2017/0224300 A1 | 8/2017 | Ishii et al. |
| 2018/0161103 A1 | 6/2018 | Wang et al. |
| 2019/0267142 A1 | 8/2019 | Wekel et al. |
| 2019/0389038 A1* | 12/2019 | Sorensen ............ B25B 23/0021 |
| 2020/0367871 A1* | 11/2020 | Van Hoven ....... A61M 25/0147 |

* cited by examiner

SYSTEM AND METHOD OF EVALUATING FLUID AND AIR FLOW

CROSS-REFERENCE TO RELATED APPLICATIONS

This application is a continuation of International Application No. PCT/2020/052567, filed Sep. 24, 2020, which claims the benefit of and priority to U.S. Provisional Patent Application No. 62/905,814, filed Sep. 25, 2019, the entire contents of each of which are incorporated herein by reference.

BACKGROUND

Field

This application relates to evaluation of fluid and/or air flow through an anatomical structure in a patient's anatomy. In some aspects, this application relates specifically to determining a degree of obstruction in a fluid or air passageway of the anatomical structure, such as a valve, artery, vein, tract, airway, etc.

Description of the Related Technology

For many cardiac, cardiovascular, and/or respiratory conditions, the incorporation of prosthetic devices into a patient's anatomy is becoming a common treatment option. However, the presence of such a device in the heart, in a blood vessel, or in a part of the respiratory tract may disrupt, or partially or entirely obstruct, the natural flow of blood or air. For example, in treatments such as transcatheter mitral valve replacement (TMVR), mitral valve-in-valve (ViV), valve-in-ring (ViR), and valve-in-MAC (ViMAC) procedures, obstruction of the left-ventricle outflow tract (LVOT) is a potentially lethal complication.

For example, TMVR, ViV, ViR, and calcific mitral valve procedures can lead to an elongation of the LVOT. This elongation is confined by the deflected anterior mitral valve leaflet, deflected bioprosthetic leaflets, and/or transcatheter heart valve struts. That is, incorporation of a prosthetic device may deflect the anterior mitral valve leaflet and may cause it to remain open, thereby at least partially obstructing the natural flow of blood from the LVOT.

Pre-procedural evaluations of a patient may be performed to estimate whether and to what degree a prosthetic device may disrupt the natural flow of blood or air in the patient. For example, a pre-procedural evaluation of possible obstructions of blood flow from the LVOT may be performed using a two-dimensional (2D) cardiac computed tomography (CT) image. Using the CT image, measurements can be made at cross-sections of the LVOT to determine a smallest cross-section of the LVOT area.

However, this procedure presents several shortcomings. For example, 2D CT images are limited to a cross-section of any anatomical region of concern. For instance, an LVOT area may include irregularities in the shape and size that cannot be seen in a 2D CT image. Thus, an irregular shape of the LVOT not shown in the 2D CT image reduces the quality of the pre-procedural evaluation. Moreover, the procedure is performed manually, leaving room for inter-user and intra-user variability and error. For example, due to the complex three-dimensional shape of the heart, manually determining the LVOT and the extent of a possible obstruction of the LVOT is not a straightforward task.

SUMMARY

Certain aspects relate to a method for evaluating fluid flow. The method includes generating a model of a structure based on a plurality of images of the structure, the structure comprising at least one fluid flow path. The method may also include identifying an obstruction element in the model of the structure, the obstruction element affecting the at least one fluid flow path in the model. The method may also include determining a region of the at least one fluid flow path for flow analysis. The flow analysis includes defining a guide curve along at least a portion of the at least one fluid flow path. The fluid analysis also includes defining a plurality of planes along the guide curve, each of the plurality of planes orthogonal to the guide curve and intersecting the region to define at least some of a plurality of cross-sections of the region. The fluid analysis also includes determining which one of the plurality of cross-sections has a smallest surface area. The fluid analysis also includes displaying a size of the smallest surface area.

Certain aspects relate to an apparatus for evaluating fluid flow. The apparatus includes a memory and a processor communicatively coupled to the memory. The processor and the memory are configured to generate a model of a structure based on a plurality of images of the structure, the structure comprising at least one fluid flow path. The processor and the memory are configured to identify an obstruction element in the model of the structure, the obstruction element affecting the at least one fluid flow path in the model. The processor and the memory are configured to determine a region of the at least one fluid flow path for flow analysis. The flow analysis includes defining a guide curve along at least a portion of the at least one fluid flow path. The flow analysis includes defining a plurality of planes along the guide curve, each of the plurality of planes orthogonal to the guide curve and intersecting the region to define at least some of a plurality of cross-sections of the region. The flow analysis includes determining which one of the plurality of cross-sections has a smallest surface area. The flow analysis includes displaying a size of the smallest surface area.

Certain aspects relate to a non-transitory computer-readable storage medium that stores instructions that when executed by a processor of an apparatus cause the apparatus to perform a method for evaluating fluid flow. The method includes generating a model of a structure based on a plurality of images of the structure, the structure comprising at least one fluid flow path. The method includes identifying an obstruction element in the model of the structure, the obstruction element affecting the at least one fluid flow path in the model. The method includes determining a region of the at least one fluid flow path for flow analysis. The flow analysis includes defining a guide curve along at least a portion of the at least one fluid flow path. The flow analysis includes defining a plurality of planes along the guide curve, each of the plurality of planes orthogonal to the guide curve and intersecting the region to define at least some of a plurality of cross-sections of the region. The flow analysis includes determining which one of the plurality of cross-sections has a smallest surface area. The flow analysis includes displaying a size of the smallest surface area.

DETAILED DESCRIPTION OF CERTAIN INVENTIVE EMBODIMENTS

As noted above, incorporation of prosthetic devices into a patient's anatomy may cause obstruction of blood and/or air pathways. In one example, a prosthetic mitral valve may cause obstruction of the left-ventricle outflow tract (LVOT), thereby reducing blood flow leaving the heart towards the aorta. Here, a prosthetic mitral valve such as a transcatheter mitral valve replacement (TMVR) may change the size and shape of the original LVOT to a modified LVOT. For example, the LVOT may be extended into the left ventricle (the extension referred to herein as a "neo-LVOT"). The neo-LVOT may have a reduced cross-section as compared to the original LVOT due to a protrusion of the prosthetic mitral valve into the LVOT.

The amount of fluid (e.g., blood) or air flow through a volume (e.g., valve, vein, artery, LVOT, neo-LVOT, airway, etc.) may be directly related to the minimum cross-sectional area through which the fluid or air flows in the volume as the minimum cross-sectional area may act as the bottleneck for flow through the volume. Accordingly, blood flow through the modified LVOT may be directly related to the minimum cross-sectional area of the neo-LVOT.

Adequate blood flow through the modified LVOT is critical to ensuring patient viability after insertion of the prosthetic mitral valve. Without adequate blood flow, the patient could have complications, which may even lead to death. Accordingly, robust pre-procedural evaluation of a neo-LVOT area can help reduce the chance of complications in a mitral valve replacement by helping to indicate the blood flow through the neo-LVOT prior to the mitral valve replacement. It should be noted that although many of the examples discussed herein relate to pre-procedural evaluations for replacing a patient's mitral valve with a prosthetic device, the techniques described herein are also applicable to pre-procedural evaluations performed prior to any other suitable procedures such as other cardiac, cardiovascular or pulmonary procedures, in which the flow of a fluid (e.g., blood), air, or another gas or liquid may be partially or entirely obstructed. Moreover, the techniques disclosed may apply with equal force to evaluation of the effect of non-medically introduced phenomena on fluid and air flow, such as stenosis, blood clots, tumors, etc.

Figure 1:
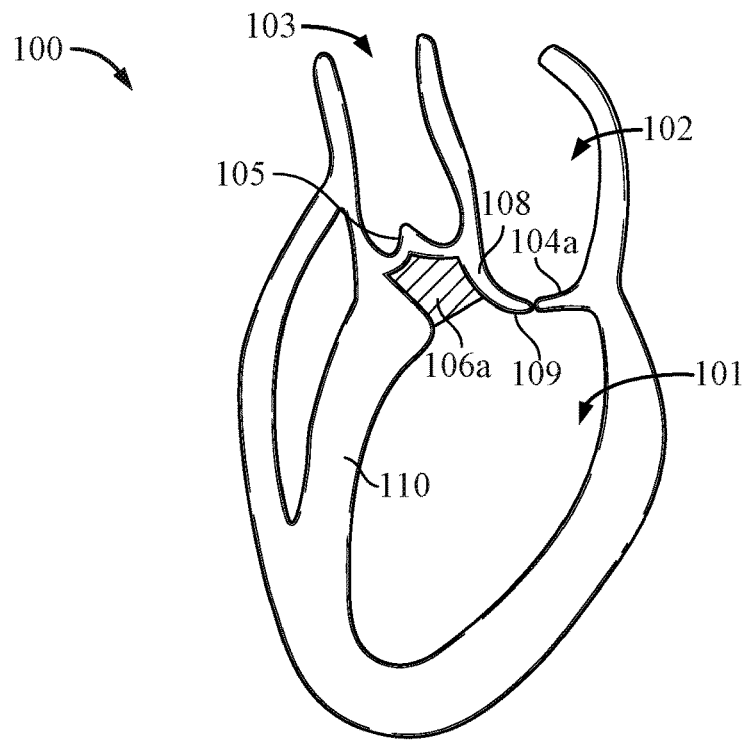
FIGS. 1 and 2 are diagrams illustrating a cutaway view of a heart.
Figure 2:
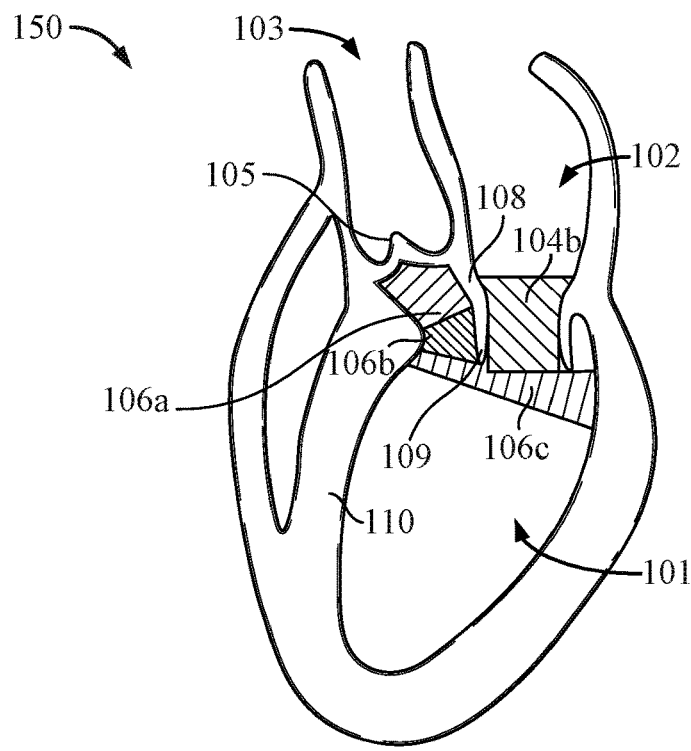

FIG. 1 is a diagram illustrating a sectional view of an example heart structure 100. In particular, the aorta 103, left ventricle 101, and left atrium 102 of heart 100 are shown. The heart structure further includes an aortic valve 105, a left ventricle outflow tract (LVOT) 106a, an intervalvular fibrosa 108, a mitral valve 104a, an anterior mitral valve leaflet (AML) 109, and an interventricular septum (IVS) 110. FIG. 2 is a diagram illustrating a sectional view of another example heart structure 150. In this example, the heart structure 150 includes a prosthetic mitral valve 104b. The placement of the mitral valve 104b in the heart 150 deflects AML 109. The deflected AML 109, along with the anatomy of the IVS 110, defines a neo-LVOT 106b. Optionally, another neo-LVOT region 106c may be added if a user determines that additional measurements are required.

In some methods, the neo-LVOT area is visually estimated by a user by first placing a schematic representation of prosthetic valve 104b in one or more 2D images, and by drawing a 2D curve along an estimate of a centerline of the modified LVOT (i.e. the combination of the original LVOT 106a, the neo-LVOT 106b, and optionally, another neo-LVOT region 106c) on one or more 2D images. The sidewall of prosthetic valve 104b is often assumed to represent the shape of the deflected AML 109. The drawing of this pseudo-centerline may be done manually by a user, and can be prone to error due to the inaccurate visual estimation. The user may then draw a plane that is perpendicular to the pseudo-centerline. The user may select the position of the plane manually at what visually appears to be a small cross-section. A distance from the intervalvular fibrosa 108, deflected AML 109 or side wall of prosthetic valve 104b to the wall of the IVS 110 along the plane is then calculated and used as an estimate of the minimum neo-LVOT area. Thus, such an evaluation of the neo-LVOT 106b is crude and may not result in an accurate determination of the minimum neo-LVOT area. For example, multiple visual estimates of the minimum neo-LVOT area for the same heart 100 with the same prosthetic mitral valve 104b placed in the same position may widely vary depending on the user making the estimation and on the choice of 2D image on which the estimation is based. Inaccurate estimations may lead to improper selection and placement of a prosthetic mitral valve 104b in a patient's heart, which could lead to complications or even death.

Unlike such methods, certain embodiments of the systems and methods described herein provide robust and accurate determinations of a degree of obstruction in a fluid or air passageway of an anatomical structure of a patient. That is, certain embodiments of the systems and methods described herein improve the technological field of medical science and medical technology by efficiently and accurately calculating a minimum cross-sectional area of an anatomical region so that a proper prosthetic device can be selected and placed in the patient's anatomy such that the prosthetic device does not obstruct or reduce proper blood and/or air flow through the anatomical region.

In one example, calculating the minimum cross-sectional area of the anatomical region may include calculating one or more of an LVOT 106a and a neo-LVOT 106b/106c. Based on these calculations, a proper prosthetic mitral valve 104b can be selected and placed in a patient's anatomy while maintaining proper blood flow through the neo-LVOT 106b/106c. Such techniques improve the technological field of medical science and medical technology by reducing the chance of patient complication due to improper neo-LVOT 106b/106c calculation and prosthetic mitral valve 104b placement and selection/design. Such techniques further improve the functioning of the computing device itself that is used to calculate the minimum neo-LVOT area 106b/106c by providing an efficient and defined computing system that efficiently finds a minimum cross-sectional area in a volume.

Figure 3:
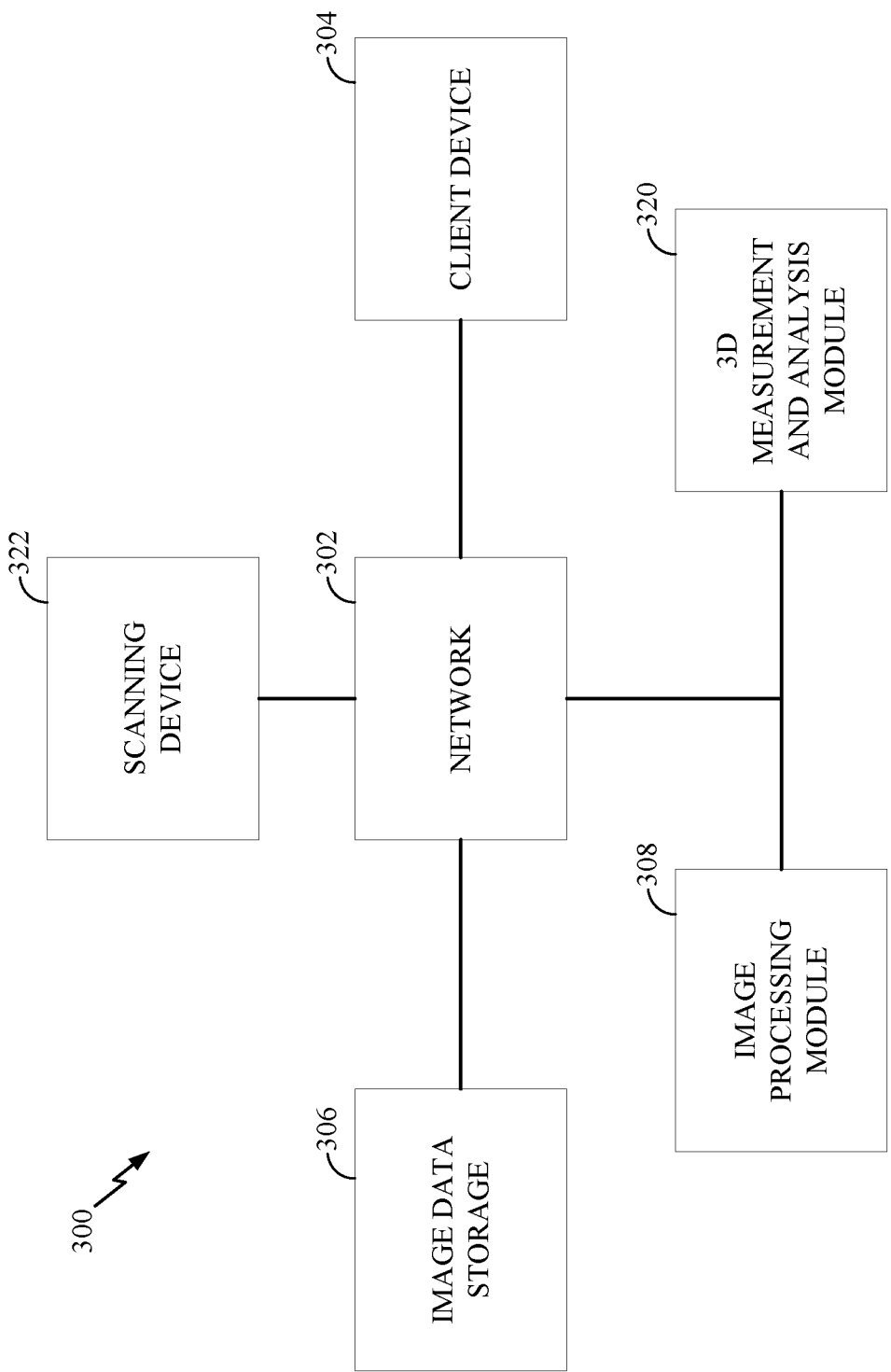
FIG. 3 is an example of a computer environment suitable for implementing certain embodiments described herein.

The systems and methods described herein may be implemented in a computing environment comprising one or more computing devices configured to provide various functionalities. FIG. 3 is an example of a computer environment 300 suitable for implementing certain embodiments described herein. The computer environment 300 may include a network 302. The network 302 may take various forms. For example, the network 302 may be a local area network (LAN) installed at a surgical site. In some embodiments, the network 302 may be a wide area network (WAN) such as the Internet. In other embodiments, the network 302 may be a combination of LANs and WANs. Typically, the network 302 will allow for secured communications and data to be shared between various computing devices. Among these computing devices are a client device 304. The client device 304 may be a typical personal computer device that runs an off-the-shelf operating systems such as Windows, Mac OS, Linux, Chrome OS, or some other operating system. The client device 304 may have application software installed to allow it to interact via the network 302 with other software stored on various other modules and devices in the computing environment 300. This application software may take the form of a web browser capable of accessing a remote application service. Alternatively, the application software may be a client application installed in the operating system of the client device 304. Client device 304 may also take the form of a specialized computer, specifically designed for medical imaging work (e.g., a specialized computer integrated in a medical-imaging appliance or the control system of a medical-imaging appliance), or even more specifically for neo-LVOT area 106b/106c determination. The client device 304 may further take the form of a mobile device or tablet computer configured to communicate via the network 302 and further configured to run one or more software modules to allow a user to perform various methods described herein.

The computer environment 300 may further include image data storage 306. Typically, the image data storage 306 takes the form of a large database designed to store image files captured by a scanning device 322. These images may be part of a digital imaging and communications in medicine (DICOM) management system, and may include 2D images (e.g., CT images), 3D images (e.g., images constructed from multiple views in 2D images), and/or 4D images. The image data storage 306 may be part of a scanning device 322, or alternatively it may be part of a client-computing device 304. The image data storage 306 may also be in a standalone database, for example in a server-based system, such as a picture archiving and communication system (PACS), having dedicated storage optimized for medical image data. The computer environment 300 may also include a scanning device 322. The scanning device 322 may typically be a medical imaging device that scans a patient to create images of their anatomy. In the computing environment 300 shown in FIG. 3, the scanning device 322 may be a CT scanner or a magnetic resonant imaging (MRI) device. However, a skilled artisan will appreciate that other suitable scanning technologies may be implemented which provide imaging data that can be used to create three-dimensional anatomical models.

As will be explained in detail below, the scanning device 322 may be configured to create cross-sectional images of a fluid or air passageway (e.g., anatomy), such as a patient's heart or airway. Those images may be stored in the image data storage 306, and utilized to create three-dimensional models of the fluid or air passageway. To that end, the computing environment 300 may also include an image processing module 308. The image processing module 308 may take the form of computer software, hardware, or a combination of both which retrieves the medical imaging data from image data storage 306 and generates a three-dimensional model, such as a 3D surface model (e.g. a 3D triangle model), using stacks of 2D image data. The image processing module 308 may be a commercially available image processing software for three-dimensional design and modeling such as the Mimics application from Materialise NV. However, other image processing software may be used. In some embodiments, the image processing module 308 may be provided via a web-based network application that is accessed by a computer over the network (such as client device 304, for example). Alternatively, the image processing module 308 may be a software application that is installed directly on the client device 304, and accesses image data storage 306 via the network 302. In general, the image processing module 308 may be any combination of software and/or hardware located within the computing environment 300 which provides image processing capabilities on the image data stored within the image data storage 306.

The computing environment also may include a 3D measurement and analysis module 320. The 3D measurement and analysis module 320 may be software that is complementary to and/or bundled with the image processing module 308. The 3D measurement and analysis module 320 may include an application configured to determine/estimate a minimum cross-section of a fluid passageway, such as neo-LVOT 106b/106c. As will be explained in further detail below, the 3D measurement and analysis module 320 may be generally used to determine precise measurements of various aspects of the fluid or air passageway (e.g., patient anatomy) and a simulated positioning of a feature in the passageway (e.g., obstruction, narrowing, implant such as a prosthetic mitral valve 104b, etc.) in order to determine the minimum cross-section of the fluid or air passageway, such as the neo-LVOT 106b/106c. As with the image processing module 308, the 3D measurement and analysis module 320 may be a network-based application which is accessed via a web browser by one or more client devices 304. It may also be a native application installed into the operating system of a computer, such as client device 304 for example. In still other embodiments, the 3D measurement and analysis module 320 may be a network application which is run as a client/server implementation. In certain embodiments, 3D measurement and analysis module 320 may operate on the 3D model generated by image processing module 308. Alternatively or additionally, 3-D measurement and analysis module 320 may operate on image data, such as from image data storage 306. Performing measurements on image data, in certain embodiments, makes it possible to eliminate the step of generating a three-dimensional model. However, performing measurements on a 3D model may produce more accurate results, as features such as centerlines and cross-sections of anatomical structures may be more accurately determined and detrimental effects of noise or other artefacts in the image data may be reduced.

Figure 4:
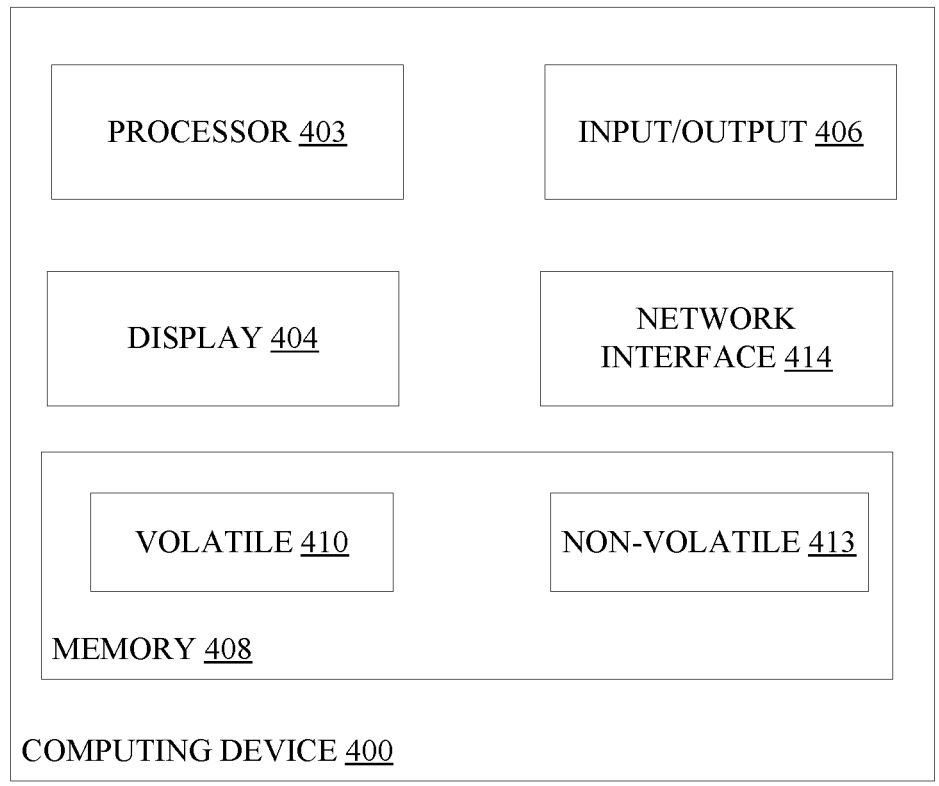
FIG. 4 is an example of a computing device suitable for implementing various embodiments is shown.

Various embodiments may be implemented using general and/or special purpose computing devices. Turning now to FIG. 4, an example of a computing device 400 suitable for implementing various embodiments is shown. The computer system 400 may generally take the form of computer hardware configured to execute certain processes and instructions in accordance with various aspects of one or more embodiments described herein. The computer hardware may be a single computer or it may be multiple computers configured to work together. The computing device 400 includes a processor 403. The processor 403 may be one or more standard personal computer processors such as those designed and/or distributed by Intel, Advanced Micro Devices, Apple, or ARM. The processor 403 may also be a more specialized processor designed specifically for image processing and/or analysis. The computing device 400 may also include a display 404. The display 404 may be a standard computer monitor such as, an LCD monitor as is well known. The display 404 may also take the form of a display integrated into the body of the computing device, for example as with an all-in-one computing device or a tablet computer.

The computing device 400 may also include input/output devices 406. These may include standard peripherals such as keyboards, mice, printers, and other basic I/O software and hardware. The computing device 400 may further include memory 408. The memory 408 may take various forms. For example, the memory 408 may include volatile memory 410. The volatile memory 410 may be some form of random access memory, and may be generally configured to load executable software modules into memory so that the software modules may be executed by the processor 403 in a manner well known in the art. The software modules may be stored in a nonvolatile memory 413. The non-volatile memory 413 may take the form of a hard disk drive, a flash memory, a solid-state hard drive or some other form of non-volatile memory. The non-volatile memory 413 may also be used to store non-executable data, such database files and the like. In some examples, computing device 400 may include non-transitory computer readable media having code stored thereon for performing the techniques and methods described herein.

The computer device 400 also may include a network interface 414. The network interface may take the form of a network interface card and its corresponding software drivers and/or firmware configured to provide the system 400 with access to a network (such as the Internet, for example). The network interface card 414 may be configured to access various different types of networks, such as those described above in connection with FIG. 3. For example, the network interface card 414 may be configured to access private networks that are not publicly accessible. The network interface card 414 may also be configured to access wireless networks such using wireless data transfer technologies such as EVDO, WiMax, or LTE network. Although a single network interface 414 is shown in FIG. 4, multiple network interface cards 414 may be present in order to access different types of networks. In addition, a single network interface card 414 may be configured to allow access to multiple different types of networks.

In general, the computing environment 300 shown in FIG. 3 may generally include one, a few, or many different types of computing devices 400 which work together to carry out various embodiments described below. For example, image data storage 306 may be part of a server-based system, such as a PACS system, and may be accessible to the image processing module 308 and/or the 3-D measurement and analysis module 320 through network interface 414. A skilled artisan will readily appreciate that various different types of computing devices and network configurations may be implemented to carry out the inventive systems and methods disclosed herein.

Data Acquisition

In certain embodiments, a user, such as a clinician, engineer, technician, etc., may use a computing device to acquire data. The data may include one or more images of the area of the fluid or air passageway (e.g., anatomy of the patient) to be evaluated. The images may include any suitable (e.g., medical) images for viewing the fluid or air passageway (e.g., computed tomography (CT) scans, etc.). The images may be contrast-enhanced images, such as angiographic images. In some examples, the images may be two-dimensional (2D), three-dimensional (3D), or four-dimensional (4D) images. The 4D images may cover a particular duration of time, such as an entire or partial heart cycle. The 2D or 3D images may include a momentary snapshot of the fluid or air passageway (e.g., end-systole anatomy of the heart structure).

In some examples, the computing device 400 may be used to display the images such that a structure of interest, such as in the patient's anatomy, can be visualized. For example, in the case of TMVR, the structure of interest may be a heart, it may be a left ventricle (e.g., the left ventricle 101 of FIG. 1) of a heart, possibly including the mitral valve and the aortic valve (e.g., the mitral valve 104a and the aortic valve 105 of FIG. 1), or it may be the left side of a heart. In some examples, the computing device 400 may be used to create a virtual 3D model of the structure of interest. For example, based on the CT images, a 3D surface model may be created of the blood pool volume of the heart or a portion thereof (e.g., the left side of the heart or the left ventricle), of any calcifications, of another portion of the anatomy, and/or of any prosthetic devices already present in the patient. Such a 3D surface model may be created by segmenting CT images. In other examples, the visualization of the structure of interest may include one or more 2D (e.g., medical) images, multi-planar reconstruction (MPR) images, or volume-rendered (e.g., medical) images. In some examples, the visualization of the structure of interest may include a display of any combination of 2D, 3D, or 4D images.

Figure 5:
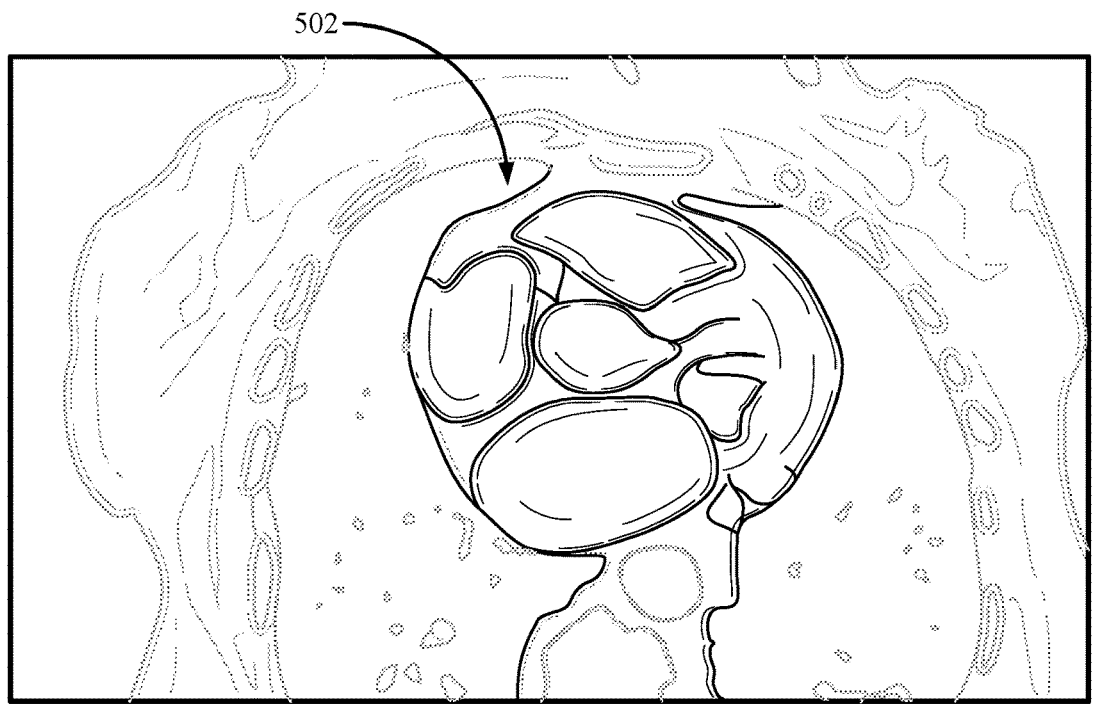
FIG. 5 is an example two-dimensional (2D) computed tomography (CT) image of a patient's heart.
Figure 6:
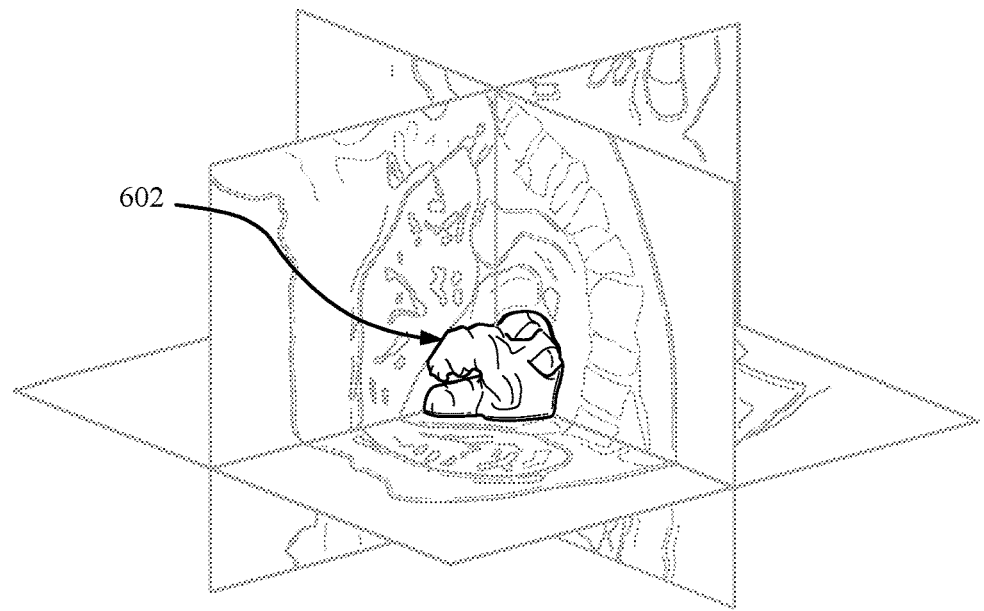
FIG. 6 is an example of a combination of multiple orthogonal 2D images that are used to generate a three-dimensional (3D) model of the patient's heart.

FIG. 5 is an example 2D CT image of a patient's heart 502. As noted, multiple 2D images may be captured of the patient's heart 502 from different perspectives or at different locations in order to generate a 3D model of the heart 502 or a portion thereof. For example, FIG. 6 is an example of a combination of multiple orthogonal 2D images that are used to generate a 3D model 602 of a structure of interest, such as the patient's heart 502 or part of the patient's heart. In this example, the image processing module of FIG. 3 may be used to fetch the images from image data storage 306 and combine the 2D images and generate the 3D model 602. In one example, the structure of interest includes the left ventricle 101, the mitral valve 104a, and the aortic valve 105. As such, the 3D model 602 includes a model of these elements of the patient's heart 502.

Figure 7:
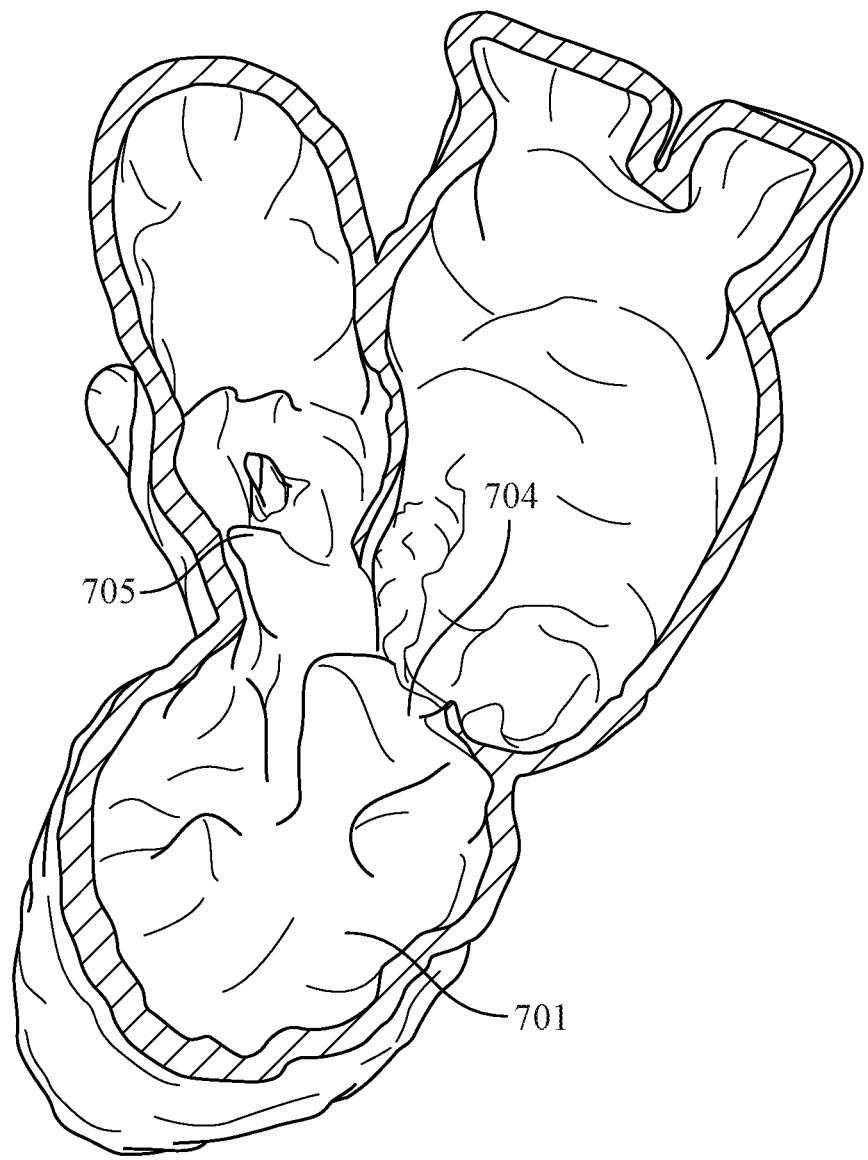
FIG. 7 is a sectional view of a structure of interest from the 3D model of FIG. 6.

FIG. 7 is a sectional view of a structure of interest 711 from the 3D model 602 of FIG. 6. In some examples, once the 3D model 602 is created, the image processing module 308 may be utilized to generate one or more sectional views of the structure of interest. In this example, the image processing module 308 uses clipping along a plane perpendicular to the mitral valve 704 and the aortic valve 705 so that a user can view the inside of the left ventricle 701. In some examples, the display of the structure of interest 711 may be adapted to reflect a planned post-treatment condition. That is, a user may adapt a graphic representation of the structure of interest 711 to include a virtual model of an implant, such as a prosthetic device.

Figure 8:
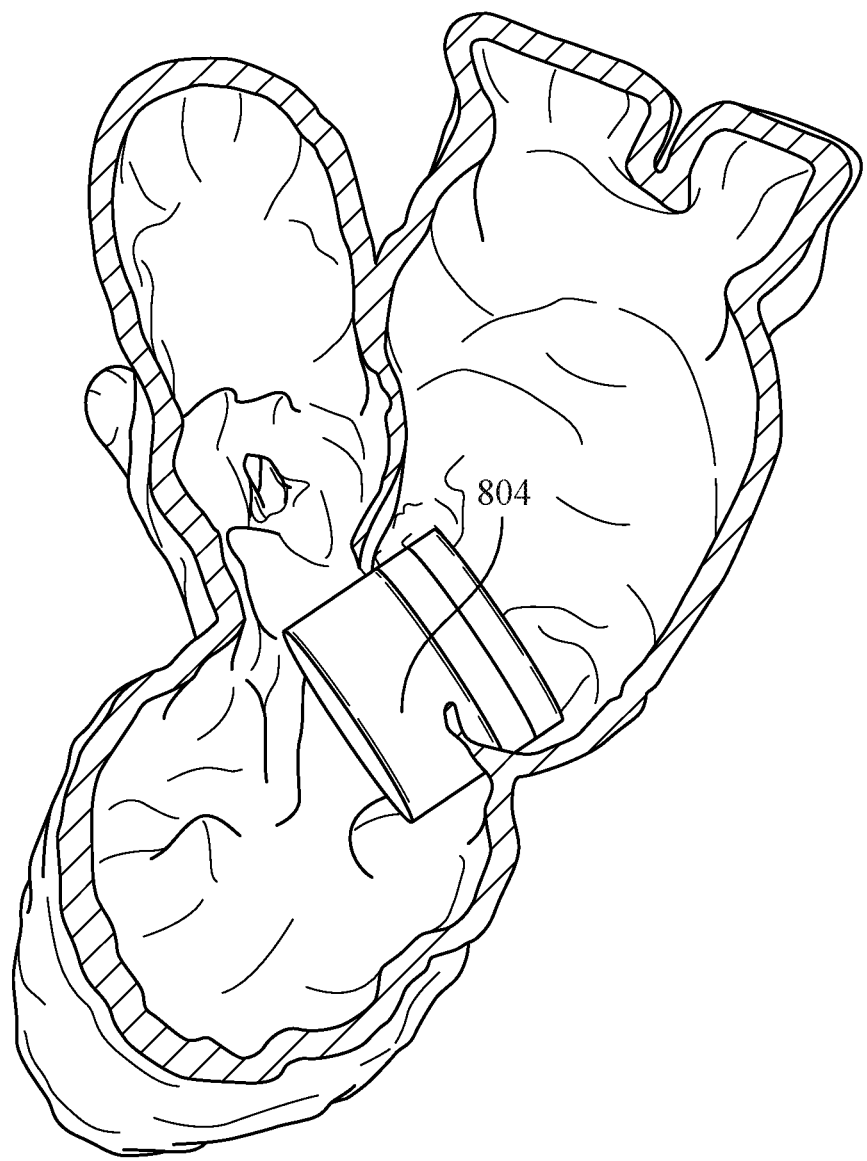
FIG. 8 is a sectional view of a structure of interest from the 3D model of FIG. 6.

FIG. 8 is a sectional view of a structure of interest 711 from the 3D model 602 of FIG. 6. In this example, the graphic representation of the structure of interest 711 has been adapted to include a virtual model of a prosthetic device 804 (in this example, a prosthetic mitral valve). In some examples, the virtual model of the prosthetic device 804 may be shaped based on its brand, type, and size. In some examples, the adaptation of the graphic representation of the structure of interest 711 may be made based on a planned orientation and location of the prosthetic device 804 relative to the structure of interest. The virtual model of the prosthetic device 804 may be a 2D or 3D model of the prosthetic device 804. It is incorporated into one or more 2D medical images and/or a virtual 3D model of the structure of interest. The virtual model of the prosthetic device 804 may include a schematic representation, such as a cylinder, or a more lifelike 3D model of the actual device. It may be a parameterized virtual object, a model loaded from a file, or a model loaded from a library of device templates.

The virtual placement of the prosthetic device 804 within the patient's anatomy may correspond to the planned outcome of the treatment. For example, a treatment outcome may be planned prior to data acquisition, and may be used to verify legitimacy of the treatment plan through virtual placement of the prosthetic device 804 within the patient's anatomy. In some embodiments, the virtual treatment plan may be created or modified during visualization of the structure of interest 711. For example, the treatment plan may be created or modified by a user, such as a medical professional, or a non-medical professional, such as a technician or engineer, by visually or automatically identifying anatomical structures in the display, and/or based on a planning algorithm dictating prosthetic device 804 selection and location. In some examples, the device size selection and/or the selection of the position (e.g., location and orientation) of the device is made with respect to the patient's anatomy. For example, with respect to features of the patient's anatomy, to anatomical landmarks, to geometrical primitives, such as coordinate systems, planes, lines, vectors or points, derived from such features or landmarks, or to measurements taken of or among such features, landmarks or geometrical primitives. In other embodiments, the acquisition of a virtual treatment plan may comprise loading a virtual treatment plan made earlier from a file, a database or any other medium.

Determination of a Region of Interest within the Structure of Interest

Figure 9:
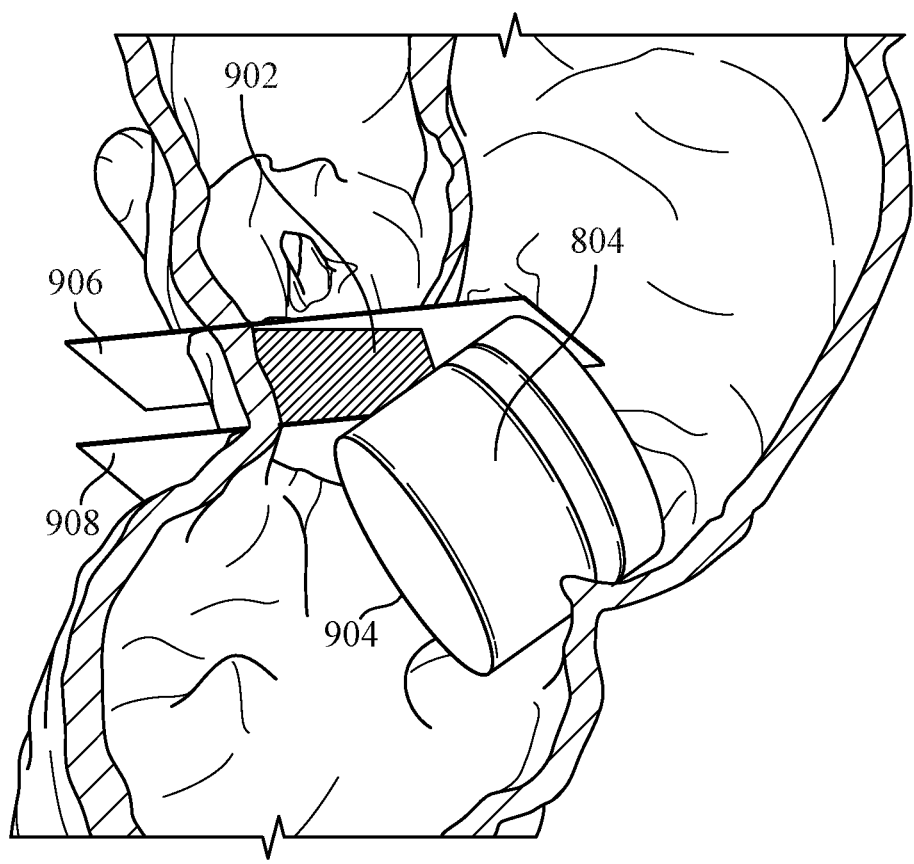
FIG. 9 is a sectional view of a structure of interest from the 3D model of FIG. 6.

FIG. 9 is a sectional view of a structure of interest 711 from the 3D model 602 of FIG. 6. In this example, the graphic representation of the structure of interest 711 has been adapted to include a 3D virtual model of a prosthetic device 804 (in this example, a prosthetic mitral valve). Here, a region of interest 902 has been determined and is visually incorporated into the structure of interest 711. In this example, the region of interest 902 lies between a first plane 906 through the aortic valve and a second plane 908 tangential to an inferior edge 904 of the prosthetic device 804. Second plane 908 may be parallel to first plane 906.

The computing device 400 may be used to determine the region of interest 902 using the displayed structure of interest 711 with prosthetic device 804. In some examples, the region of interest 902 may be visually determined by a user and/or an algorithm. For example, the region of interest 902 may be indicated manually by the user on the depiction of the structure of interest 711 (e.g., prior to incorporation of the prosthetic device as shown in FIG. 7) or on the adapted depiction of the structure of interest (e.g., after incorporation of the prosthetic device as shown in FIGS. 8 and 9). In another example, the region of interest may be determined automatically by an algorithm based on, for example, manually or algorithmically identified anatomical structures in the structure of interest 711 and/or surrounding areas. For example, first plane 906 may be determined as the best-fit plane through the annulus of the aortic valve. The annulus may be indicated manually by a user on one or more depictions of the structure of interest 711, or may be detected automatically using any suitable feature-recognition technique known in the art.

The region of interest 902 may encompass the entire structure of interest 711, or only a part of the structure where the obstruction of the fluid flow may be expected. In some examples, the region of interest 902 may include the LVOT 106a and/or the neo-LVOT 106b/106c, which together are confined by the aortic valve, the basal septum, the intervalvular fibrosa, and the deflected anterior mitral valve leaflet. In some examples, the deflected anterior mitral valve leaflet may be approximated by the user or algorithm by identifying the outer wall of the representation of the prosthetic device. In some examples, the region of interest 902 may encompass the entire left ventricle, optionally excluding the volume occupied by the 3D virtual model of a prosthetic device 804.

One example of a process for determining the region of interest 902 may include the following steps: (i) a user may utilize image processing module 308 or measurement and analysis module 320 (e.g., Mimics application from Materialise NV, 3D Slicer, etc.) on the computing device 400 to detect and indicate structural elements (e.g., aortic valve) of a 2D image or a 3D/4D model, either manually or utilizing 2D and/or 3D feature recognition algorithms with or without an initial visual identification of structural elements by a user (e.g., a user may provide an initial indication of what structural aspects, such as the aortic valve annulus, correspond to which portions of the model or image); (ii) upon recognition of the structural aspects, an algorithm may insert the first plane 906 through the aortic valve of the displayed structure of interest 711; (iii) the first plane 906 may be translated into the left ventricle until it is tangential with an inferior edge 904 of the prosthetic device 804. In this example, the translated first plane is displayed on the structure of interest 711 as a second plane 908. In this case, the region of interest 902 may be limited to the section of an adapted blood pool volume (e.g., the blood pool volume minus the volume of the representation of the prosthetic device 804) between the aortic valve or the first plane 906 and the second plane 908. In some embodiments, steps (i) and/or (ii) may be replaced by the user manually indicating the first plane 906. For example, the user may indicate three points on the structure of interest 711 (e.g., the aortic cusps) through which the first plane may be drawn.

In some embodiments, the region of interest 902 may extend into the left atrium to include more than the LVOT and neo-LVOT (e.g., the neo-LVOT extension 106c of FIG.

Figure 10:
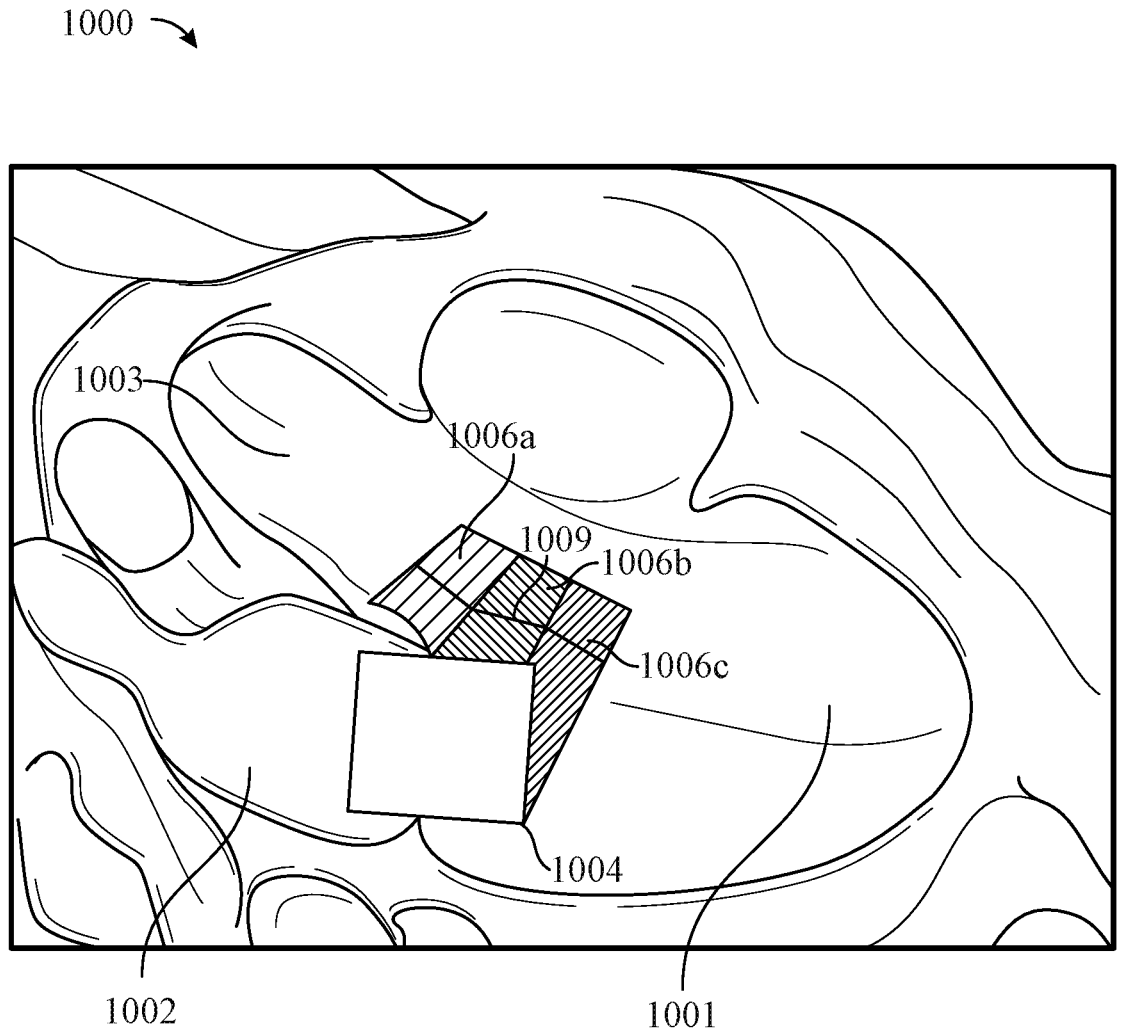
FIG. 10 is a sectional view of an example 2D CT image of a patient's heart.

1). FIG. 10 is a sectional view of an example 2D CT image of a patient's heart 1000. In this example, the 2D CT image includes a sectional view of the left ventricle 1001, the left atrium 1002, the aorta 1003, a virtual model of a prosthetic device 1004 (e.g., note that the virtual model is a 2D model for implementation in a 2D image), an LVOT 1006a, a neo-LVOT 1006b, an extension 1006c of the neo-LVOT, and a centerline or guide curve 1009 of the LVOT 1006a, the neo-LVOT 1006b, and the extension 1006c. In this example, the region of interest (e.g., the combination of the LVOT 1006a, the neo-LVOT 1006b, and the extension 1006c) may further include a volume that is bound by a plane that is tangential with an inferior edge 904 of the representation of the prosthetic device 804 on the posterior side.

Other boundaries may also be defined. For example, a 2D or 3D guide curve 1009 through (part of) the structure of interest, including or excluding the volume occupied by the representation of the prosthetic device 1004, may be indicated by the user or may be calculated by an algorithm. For example, the guide curve may be calculated as a centerline through the left ventricle and the aorta. That is, in some embodiments, a centerline of a flow path may be calculated using the boundaries of the structure of interest, such as the lumen of the vessel through which fluid flows, to determine the center of the flow path. In this example, the centerline may be bounded by the intervalvular fibrosa and the basal septum, meaning that the centerline is equidistant to both structural elements. For obtaining a 2D guide curve, a 2D centerline may be calculated based on a 2D representation of the structure of interest (e.g., a 2D medical image). For obtaining a 3D guide curve, a 3D centerline may be calculated based on a 3D representation of the structure of interest (e.g., a 3D model, such as a surface model). As discussed above, performing these steps in 3D will yield more reliable results, as it allows taking the full three-dimensional shape of the anatomy into account. Next, a plane perpendicular to this guide curve 1009 may be determined as the boundary opposite the fluid flow exit (e.g. the aortic valve) of the structure of interest. In example, this may be a plane perpendicular to the guide curve 1009 and tangential to an inferior edge of the representation of the prosthetic device 1004 on the side nearest the fluid flow exit (e.g., the anterior side). In another example, this may be a plane perpendicular to the guide curve 1009 and tangential to an inferior edge of the representation of the prosthetic device 1004 on the side farthest the fluid flow exit (e.g., the posterior side). In yet another example, this may be a plane perpendicular to the guide curve 1009 at another location (e.g., tangential to the native mitral valve annulus on the anterior or posterior side).

In some embodiments, calcifications and/or pre-existing hardware are subtracted from the blood pool volume or part of the blood pool volume to determine the region of interest. Thus, a region of interest (e.g., an LVOT 1006a, a neo-LVOT 1006b, and/or an extension 1006c) may be defined mentally by the user, or may be stored as a separate virtual entity or collection of entities. In some examples, the region of interest is stored as a virtual 3D model, such as a virtual 3D surface model (e.g., as a virtual 3D surface model of the anatomical structure of the LVOT 1006a, the neo-LVOT 1006b, and/or the extension 1006c). In other examples, the region of interest may be stored as one or more planes, curved surfaces, polygons, triangles, lines, curves, splines, cylinders or other geometrical primitives delimiting a section of the structure of interest. In some embodiments, the region of interest and/or its limits may be visualized instead of, in addition to or overlaid onto the adapted depiction.

Defining a Guide Curve Through the Region of Interest

Figure 11:
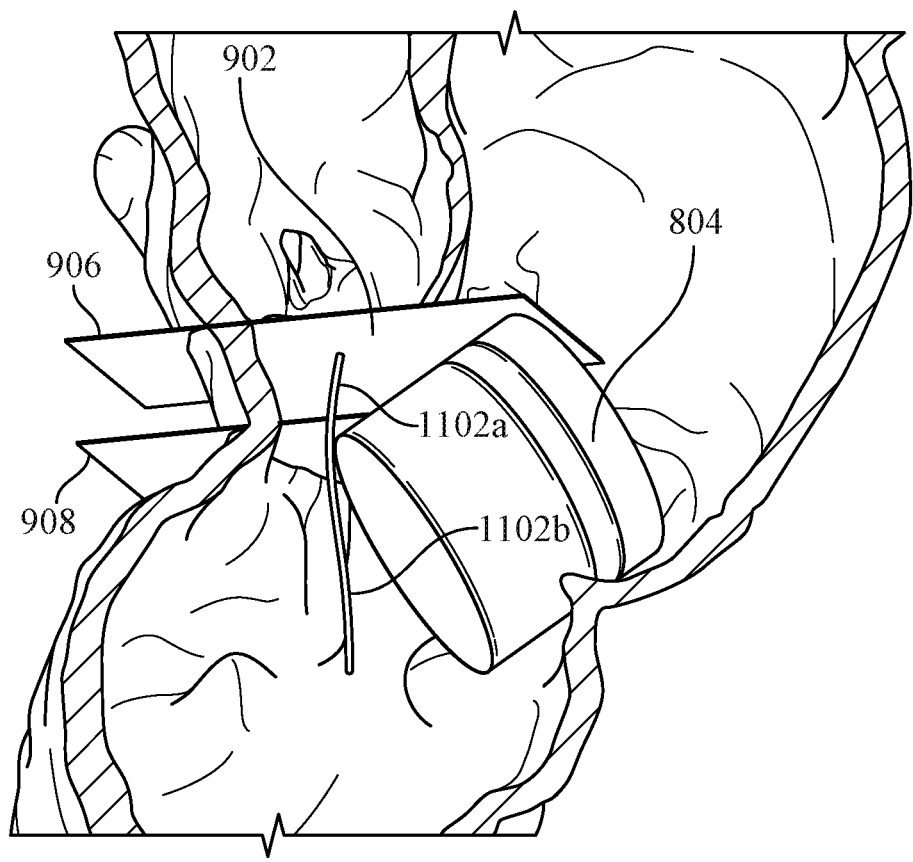
FIG. 11 is a sectional view of a structure of interest from the 3D model of FIG. 6.

FIG. 11 is a sectional view of a structure of interest 711 from the 3D model 602 of FIG. 6. In this example, a guide curve 1102 has been determined and visually adapted to the structure of interest 711. Here, the guide curve 1102 includes a first portion 1102a being a centerline of the region of interest (e.g., the LVOT 1006a and the neo-LVOT 1006b of FIG. 10), and a second portion 1102b being a centerline of an extension of the region of interest (e.g., the extension 1006c of FIG. 10). In some examples, a location and direction of a guide curve 1102 may be determined, and a graphic representation of the guide curve 1102 incorporated into the depiction of the structure of interest 711 (e.g., prior to incorporation of the prosthetic device) or on the adapted depiction of the structure of interest (e.g., after incorporation of the prosthetic device). The guide curve 1102 may be determined based on characteristics of the region of interest (e.g., the guide curve may include a centerline of the region of interest). Centerlines may be calculated automatically using any suitable centerline algorithms known in the art. Robustness of certain of these algorithms may be improved by applying them on an extended region of interest (e.g. incorporating the neo-LVOT extension 1006c, or extending even further into the left ventricle or into the aorta).

In another example, the guide curve 1102 may be generated between two points selected by the user or an algorithm. For example, the user may arbitrarily select two points on a displayed structure of interest 711. Alternatively, an algorithm may select two points at opposite ends of the structure of interest 711 or region of interest. In this case, the algorithm may select the two points such that both points are centered in a fluid or air flow path (e.g., in this example, the left ventricle). In other examples, a first point may be: (i) an arbitrary point in the structure of interest 711, (ii) a manually indicated point in the structure of interest 711, (iii) an anatomical landmark of the structure of interest 711 (e.g., the apex of the left ventricle), or (iv) the center of the region of interest, either including or excluding the volume of the representation of the prosthetic device 804 (e.g., the center of gravity of the blood pool volume of the left ventricle, optionally excluding the volume of the prosthetic device 804 in its planned position, any calcification, and/or any pre-existing hardware). A second point may be a point near the fluid flow exit of the structure of interest 711, such as an arbitrary point near the aortic valve, a manually indicated point near the aortic valve, or an automatically determined point, such as the center of the aortic valve. In some examples, multiple points may be added between the first and second points to provide the user with more control over the direction of the guide curve. In some examples, the guide curve may comprise one or more straight-line segments, and/or one or more curved segments, such as spline curves, between the selected points.

In some examples, the guide curve 1102 is manually defined by a user (e.g., the user may hand-draw the guide curve on the depiction or the adapted depiction). The user may include a medical professional or a non-medical professional, such as an engineer or a technician, or any other suitable user. Alternatively, the guide curve 1102 is determined algorithmically based on the depiction or on the adapted depiction. For example, the guide curve 1102 may be determined as a straight line between the first and second points. Alternatively, the guide curve 1102 may be determined as the centerline of the structure of interest 711 and/or region of interest, including or excluding the volume of the representation of the prosthetic device 804. In this case, the algorithm may determine the guide curve 1102 such that the guide curve 1102 follows a centerline defined by the structure of interest 711 and/or region of interest. For example, the algorithm may determine (part of) the path of the guide curve 1102 based on the walls of the aorta, such that the guide curve 1102 follows a path that is substantially centered in the blood flow path.

In some examples, instead of defining the guide curve 1102 as a centerline through the structure of interest 711 and/or region of interest, the guide curve 1102 may be defined as a straight line segment (e.g., not necessarily centered) through the structure of interest 711 and/or region of interest (e.g., along the blood flow path of the aorta). In some examples, the guide curve 1102 may be defined as a line segment (e.g., not necessarily centered or straight) through the structure of interest 711 and/or region of interest. In other examples, the guide curve 1102 may be a straight line segment or a curve, such as a spline, that substantially follows the fluid flow path from the first point to the second point.

The guide curve 1102 may be visually displayed as an object on 2D image data or on 3D/4D models. In some examples, the guide curve 1102 may be a 2D curve (e.g., fully defined in one plane and graphically represented on a single 2D image, a single MPR image, or a 3D model) or a 3D object represented on a single 2D image, a single MPR image, or a 3D/4D model.

Defining a Plurality of Evaluation Planes

As discussed, the guide curve 1102 may be a curve or line substantially following a fluid/air flow path, or may be a centerline of (part of) the structure of interest 711 or of the region of interest. In some embodiments, one or more planes may be defined and optionally visually displayed along the guide curve 1102 to determine a cross-sectional surface area of the structure of interest or region of interest. As such, the one or more planes may intersect with the surrounding anatomical structures shown in the 2D image or 3D/4D model and may define closed cross-sections through which fluid/air will flow. One or more planes orthogonal to the guide curve provide an optimal basis for the evaluation of fluid flow obstruction because a laminar flow can be expected to flow substantially parallel to the guide curve. Thus, determining the cross-sectional surface area of a particular region will provide a user with information indicative of whether a possible obstruction of the fluid/air flow will result from a prosthetic device.

Figure 12:
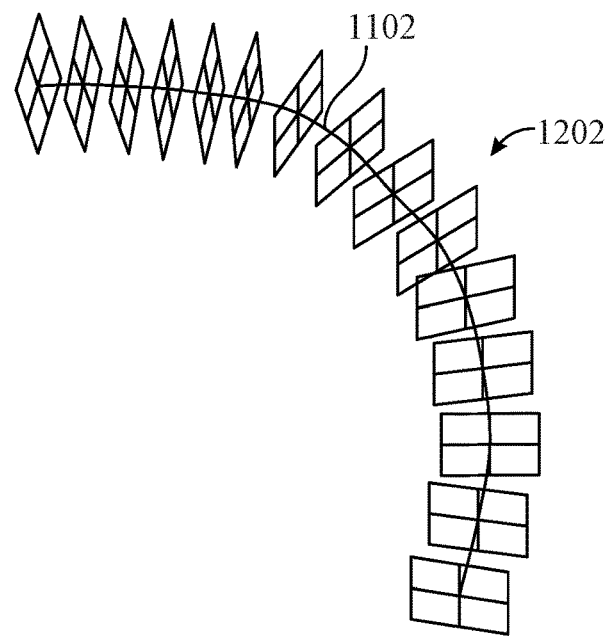
FIG. 12 is a diagram illustrating a conceptual guide curve having a plurality of planes defined orthogonally to the guide curve.

FIG. 12 is a diagram illustrating a conceptual guide curve 1102 having a plurality of planes 1202 defined orthogonally to the guide curve 1102. Here, the plurality of planes 1202 are defined orthogonal to the guide curve 1102 at (e.g., regular) intervals along the guide curve 1102. The intervals may be determined by an algorithm based on the length of the guide curve 1102, the gradient of the anatomical structure(s) along the guide curve 1102, etc. Smaller intervals may be chosen in zones where the likelihood of an obstruction is higher and vice-versa. The user may also determine the intervals to strike a balance between accuracy and computational load, such as a value between 1 mm and 2 cm (e.g., 2 mm, 3 mm, 4 mm, 5 mm, 6 mm, 7 mm, 8 mm, 9 mm, 1 cm, or 1.5 cm). The plurality of planes 1202 may constitute a plurality of evaluation planes.

It should be noted that a manually drawn guide curve 1102 may be less accurate relative to an algorithmically determined guide curve 1102, and an automatically determined guide curve 1102 may not reflect all anatomical features (e.g., local protrusions or indentations) along the anatomical boundaries (e.g., walls of an aorta or walls of a breathing passage) of the region of interest.

Figure 13:
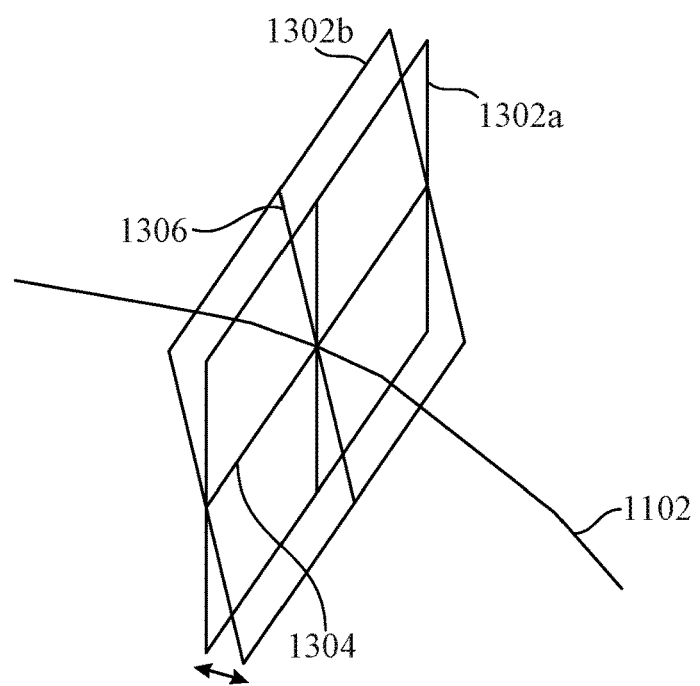
FIG. 13 is a diagram illustrating a conceptual guide curve having a first plane of the plurality of planes.

FIG. 13 is a diagram illustrating a conceptual guide curve 1102 having a first plane 1302a of the plurality of planes 1202. Note that, as illustrated in FIG. 13, the first plane 1302a refers to one of the planes 1202. Further, rotated first plane 1302b refers to a rotation of the first plane 1302a about a first axis 1304. Though not shown, additional rotations of the first plane 1302a about the first axis 1304 may be included, and each rotated position of the first plane 1302a may be added to the plurality of evaluation planes. Thus, in the context of the plurality of planes 1202 along the guide curve 1102, each of the plurality of planes 1202 are in a first position resulting in a first plurality of evaluation planes (e.g., one evaluation plane corresponding to each of the plurality of planes 1202). Yet, additional evaluation planes may be generated by incrementally rotating one or more of the plurality of planes 1202. For example, each incremental rotation of the first plane 1302a may result in an additional evaluation planes (e.g., rotated first plane 1302b).

The plurality of planes 1202 may be generated orthogonally along the guide curve 1102 and rotated about local rotation axes to provide additional evaluation planes. For example, each of the plurality of planes 1202 may be rotated about a local rotation axis in angular increments in one or more directions. In this example, the first plane 1302a may be rotated along the first axis 1304 (e.g., tangential to the first plane 1302a/locally perpendicular to the guide curve 1102) through the intersection point of the first plane 1302a and the guide curve 1102. Alternatively, or in addition, the first plane 1302a may be rotated along a second axis 1306 (e.g., tangential/locally perpendicular to the guide curve 1102 and the first axis 1304). Each plane may be rotated over one or more (e.g., fixed) angular increments, such as 1°, 2°, 5°, 10°, 12°, or 15°. After each rotation, the resulting rotated plane, e.g., plane 1302b, may be added to the plurality of evaluation planes. As such, the rotation of the first plane 1302a may result in multiple different evaluation planes.

Accordingly, the plurality of evaluation planes (e.g., a second plurality of planes) may be defined along the guide curve 1102 by rotating one or more of the plurality of planes 1202 about one or more axes tangential/perpendicular to the guide curve 1102 over one or more angular increments. In one example, one or more of the plurality of evaluation planes correspond to a first rotation of one plane (e.g., first plane 1302a) of the one or more of the plurality of planes 1202 about the first axis 1304 perpendicular to the guide curve 1102 over one or more angular increments, respectively. Thus, each of the plurality of planes 1202 and each of the plurality of evaluation planes may intersect an anatomical structure (e.g., in the region of interest) at a different location. In another example, one or more of the plurality of evaluation planes correspond to a second rotation of one plane (e.g., first plane 1302a) of the one or more of the plurality of planes 1202 about a second axis 1306 perpendicular to the guide curve 1102 and the first axis 1304. In some examples, the intersection between a plane and the anatomical structure may define a cross-section of the anatomical structure, as discussed further below.

Figure 14:
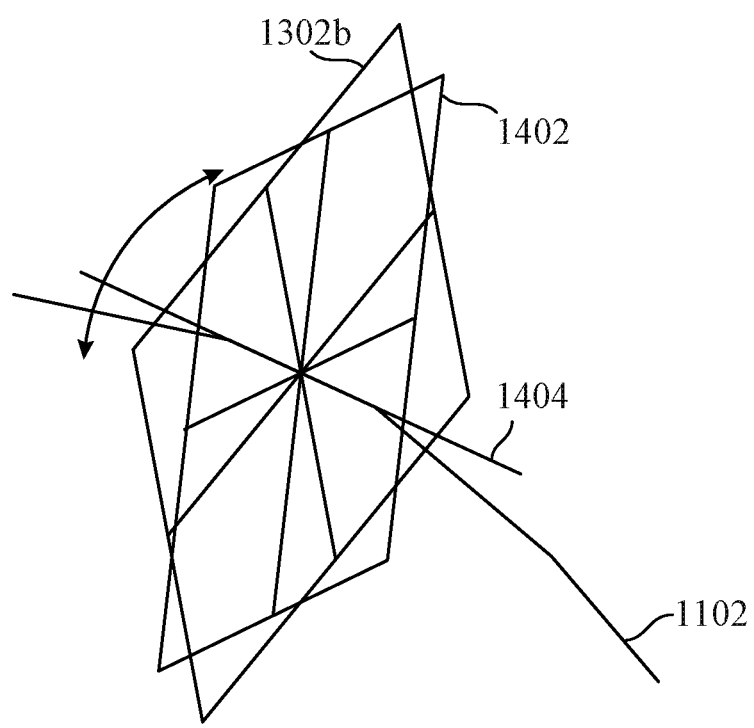
FIG. 14 is a diagram illustrating the conceptual guide curve having a rotation of the first plane of the plurality of planes.

FIG. 14 is a diagram illustrating the conceptual guide curve 1102 having the rotated first plane 1302b corresponding to a rotation of one of the plurality of planes 1202. Note that, as illustrated in FIG. 14, there is the first rotated plane 1302b and a further rotated plane 1402 corresponding to a further rotation of the rotated 1302b about a different third axis 1404, that is different than the axis about which first plane 1302a was rotated to generate rotated plane 1302b. Additional rotations may be included, and each rotation of the rotated first plane 1302b may be added to the plurality of evaluation planes. Further, any one or more rotated planes generated from any one or more of planes 1202 may similarly be further rotated along a different axis and the result added to the plurality of evaluation planes. In this example, the rotated first plane 1302b may be rotated along the third axis 1404 (e.g., tangential/locally perpendicular to the guide curve 1102 and perpendicular to the first axis 1304) through the intersection point over one or more (e.g., fixed) angular increments, such as 1°, 2°, 3°, 5°, 10°, 12°, 15°, 20°, 30°, 45° or 90°, such as making full circle (e.g., 35 rotations over 10° or 17 rotations over 20°). Accordingly, one or more of the rotations of one or more of the plurality of planes 1202 may be further rotated along a corresponding third axis 1404. Additional evaluation planes may be defined by combining rotations over zero or more angular increments over the three axes. In some examples, each rotational process may be followed by one or more additional rotational processes, where each plane is rotated in a different direction during each process. In one example, rotation of a plane about the third axis 1404 may be performed on a plane only after a rotation of that plane about the first axis 1304, the second axis 1306, and/or any additional axes. After each rotation process, the resulting planes are added to the plurality of evaluation planes.

In some examples, the 3D measurement and analysis module 320 of FIG. 3 may perform generation of the plurality of planes 1202 and guide curve 1102, as well as any plane rotation and cross-sectional measurements of each plane. By extending the plurality of evaluation planes using rotations of the planes, local inaccuracies of a manually indicated or automatically computed guide curve can be overcome, and the chance of finding the true smallest cross-section through the region of interest can be improved.

Determining a Cross-Sectional Size

In some embodiments, a surface area of a cross-section of an anatomical structure (e.g., in the region of interest) where each of the plurality of planes 1202 intersects with the anatomical structure may be determined. In one example, an algorithm may generate a segment image or shape (e.g. as a polygon, a closed polyline, or closed curve) of the intersection between each plane and the lumen of the anatomical structure through which fluid/air will flow, and then calculate the surface area of that cross-section. The same may be done for each angular increment of rotation of the plane.

For example, in an adapted depiction of a 2D image, a user or algorithm may calculate a distance from one end of where a plane intersects the anatomical structure, to another end of where the same plane intersects the other side of the anatomical structure. In another example, the adapted depiction of the structure of interest may include a 3D surface model of the region of interest, and the surface area of the cross-section of the region of interest at an evaluation plane may be determined by first determining the intersection of the evaluation plane with the anatomical structure of the 3D surface model, and by subsequently determining the surface area of that cross-section. In some examples, the determination of a surface area of a cross-section of a 3D model may be performed by an algorithm using 3D geometry operations.

Optionally, one or more evaluation planes may be discarded based on their position with respect to: (i) the representation of the prosthetic device, (ii) the structure of interest, (iii) the region of interest, or (iv) the boundaries of any of these entities. For example, as blood can be expected to flow perpendicularly to the aortic valve, all evaluation planes that intersect the aortic valve may be discarded. In another example, as fluid flow obstruction due to the placement of the prosthetic device is evaluated, all evaluation planes that do not intersect the representation of the prosthetic device may be discarded.

In some embodiments, the smallest cross-section is determined by finding the smallest surface area among all, or remaining, evaluation planes (e.g., among each of a plurality of planes and each of their rotations). This smallest surface area may be interpreted as a measure for the passageway still available for fluid/air flow after the planned medical procedure, or as a measure of a level of obstruction that will result from the planned medical procedure. The smallest surface area may be determined via an algorithm or manually by a user.

In some examples, the determination of the smallest cross-section may allow a user to approve, reject, or modify a pre-planned treatment. The methods described herein may be repeated over a plurality of virtual treatment plans in order to compare and select an optimal treatment plan (e.g., to select the type and size of prosthetic device and/or the position of the prosthetic device best suited for a patient).

In some examples, the plurality of planes defined along the guide curve may be divided into a plurality of subsets of one or more planes that share an intersection point with the guide curve. In this example, a smallest cross-section among one or more planes in a subset is determined for each subset. Accordingly, multiple cross-sections may be used to evaluate fluid/air flow in the structure of interest and/or region of interest. For example, all evaluation planes that share the same intersection point with the guide curve can be grouped in one subset (e.g., all evaluation planes that are generated by rotating a first plane about one or more axes and/or points). As such, the evolution of the minimum cross-sectional surface area may be followed along the guide curve.

Figure 15:
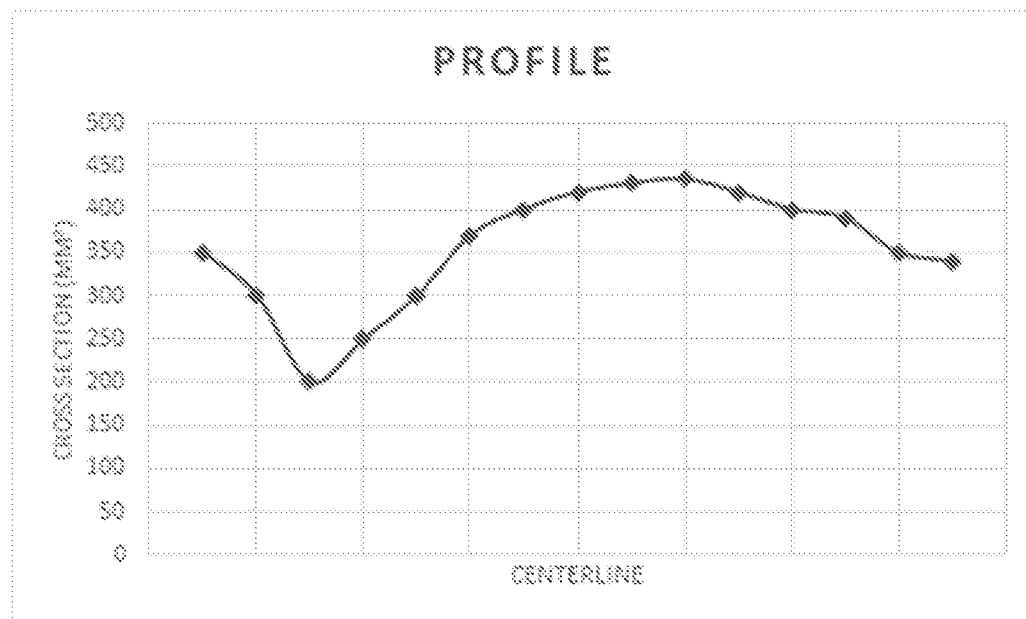
FIGS. 15 and 16 are example graphs illustrating a cross-sectional area along a centerline or guide curve of a fluid or air passageway.
Figure 16:
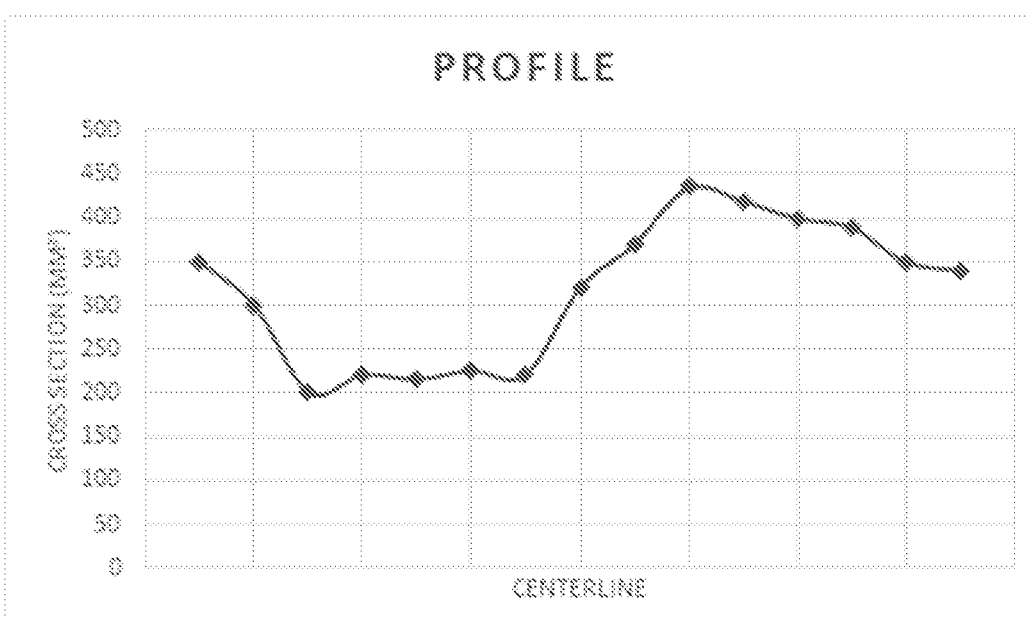

In some examples, based on a smallest surface area of each of two or more subsets along the guide curve may be graphically profiled to generate a smallest surface area profile. This provides the benefit of being able to distinguish between a discrete stenosis (e.g., a localized narrowing of the passageway) and a tunnel stenosis (e.g., a narrowing over a relatively longer distance). The multiple cross-section surface areas may be graphically profiled and presented as a graph (e.g., where the distance along the guide curve is presented along the horizontal axis, and the size of the cross-section of the anatomical structure is presented along the vertical axis. For example, both FIGS. 15 and 16 are example graphs illustrating a cross-sectional area along a centerline or guide curve of a fluid or air passageway. In this example, FIG. 15 may indicate a discrete stenosis, while FIG. 16 may indicate a tunnel stenosis.

Alternatively or additionally, cross-sectional surface areas of an anatomical structure may be graphically presented in the adapted depiction. For example, a false-color overlay on a structure of interest and/or a region of interest indicating cross-sectional sizes, where the colors of the surfaces of the 3D model are mapped to different cross-sectional sizes.

As noted above, the techniques described herein may also be used to identify a type of stenosis in an anatomical structure of a patient. In one example, a threshold value may be determined for the number of evaluation plane subsets and/or the length of the section of the guide curve along which a narrowing may be identified. A narrowing below this threshold (e.g., a small number of cross-sectional sizes in one region that are relatively smaller than other cross-sectional sizes outside of the one region) may be identified as a discrete stenosis. A narrowing above this threshold (e.g., a large number of cross-sectional sizes in one region that are relatively smaller than other cross-sectional sizes outside of the one region) may be identified as a tunnel stenosis. That is, a relatively localized or short distance of small cross-sectional sizes will likely correspond to a discrete stenosis, whereas a relatively broader distance of small cross-sectional sizes will likely correspond to a tunnel stenosis.

In some examples, cross-sectional values for both the pre-procedural (e.g., using a visual depiction of a structure of interest prior to procedure) and post-procedural situation (e.g., using a visual depiction of the structure of interest adapted with the post procedure prosthetic device) may be calculated and presented to the user. Here, the smallest cross-section may be determined in a pre-procedural situation (e.g., the smallest cross-section is determined in an original depiction of an anatomical structure, not an adapted depiction). This may result in the smallest cross-section of the LVOT. Then, the smallest cross-section may be determined in a post-procedural situation (e.g., the smallest cross-section is determined in an adapted depiction). Systems according to certain embodiments may then display the ratio of the post-procedural smallest cross-section and the pre-procedural smallest cross-section as a measure for the remaining fluid/air passageway, or as a measure of obstruction of the fluid/air passageway. For example:

$$\frac{\text{smallest cross section } (LVOT + neo-LVOT)}{\text{smallest cross section } (LVOT)},$$

$$\text{or } 1 - \frac{\text{smallest cross section } (LVOT + neo-LVOT)}{\text{smallest cross section } (LVOT)}.$$

In some examples, the system may display a ratio of a determined smallest cross-section of the region of interest and a cross-section of the pre-procedural structure in the same evaluation plane.

Figure 17:
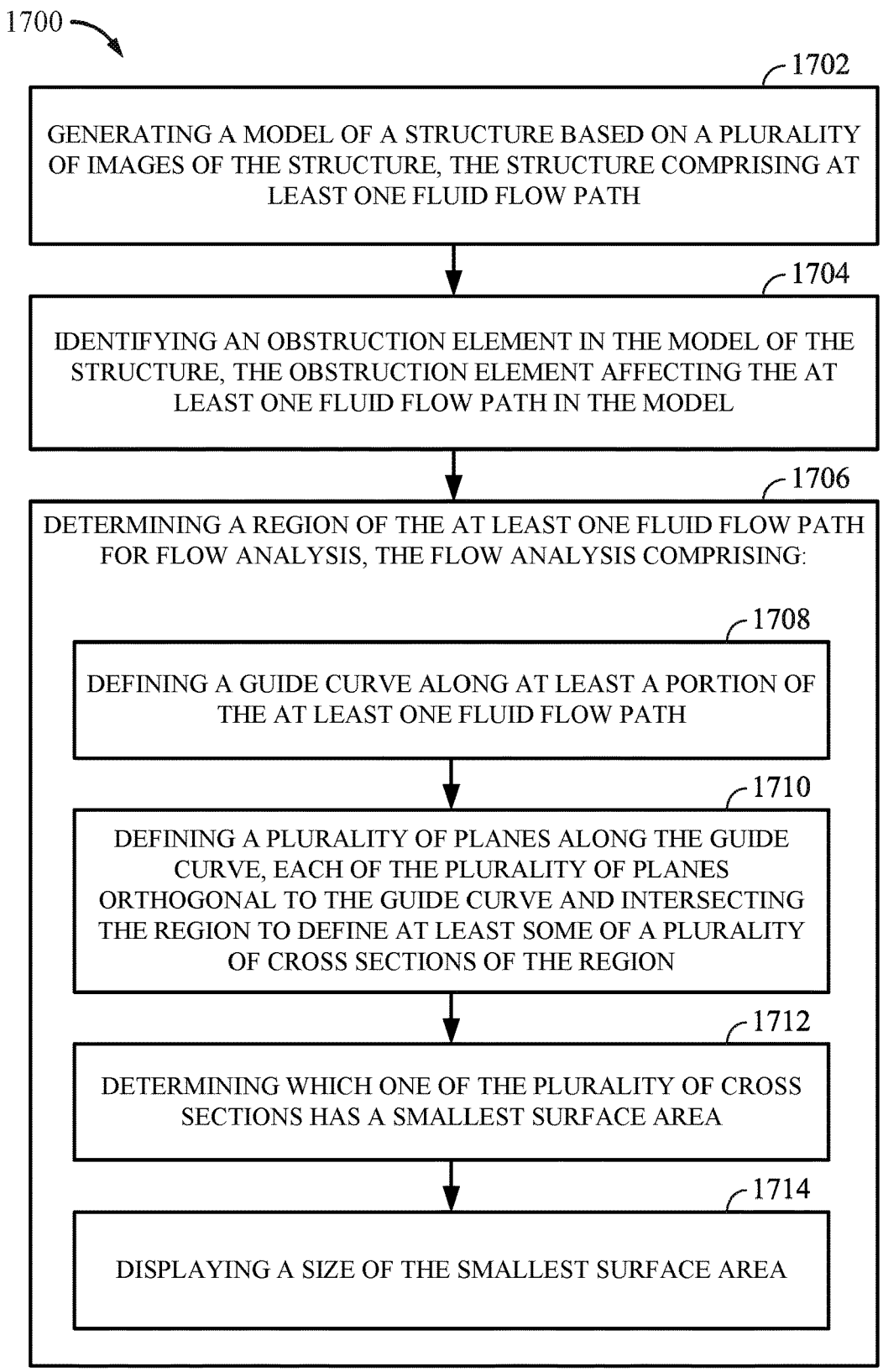
FIG. 17 is a flow chart showing a process for creating a plurality of section planes, according to certain embodiments.

FIG. 17 is a flow chart illustrating a process 1700 for determining a minimum neo-LVOT cross-sectional surface area according to certain embodiments. It should be noted that in certain embodiments, process 1700 is a computer-implemented process. Further, certain blocks may be performed automatically, manually by a user of a computing device, or partially manually and partially automatically such as based on input from a user of a computing device. The user may be a medical professional or a non-medical professional, such as a technician or an engineer. Further, certain blocks may be optional, and parts of the described method may be performed as separate methods.

Process 1700 begins at block 1702, by generating a model of a structure based on a plurality of images of the structure, the structure comprising at least one fluid flow path.

The process 1700 may proceed to block 1704 by identifying an obstruction element in the model of the structure, the obstruction element affecting the at least one fluid flow path in the model.

The process 1700 may proceed to block 1706 by determining a region of the at least one fluid flow path for flow analysis. In some examples, the flow analysis includes the processes shown in blocks 1708 through 1714. For example, the process 1700 may proceed to block 1708 by defining a guide curve along at least a portion of the at least one fluid flow path. The process 1700 may proceed to block 1710 by defining a plurality of planes along the guide curve, each of the plurality of planes orthogonal to the guide curve and intersecting the region to define at least some of a plurality of cross-sections of the region. The process 1700 may proceed to block 1712 by determining which one of the plurality of cross-sections has a smallest surface area. The process 1700 may proceed to block 1714 by displaying a size of the smallest surface area.

In some examples, the obstruction element is a virtual model of a prosthetic device inserted into the model.

In some examples, the process 1700 further includes selecting the virtual model of the obstruction element based on a treatment plan to improve fluid flow in a second fluid flow path.

In some examples, defining the guide curve includes selecting a first point at a first location of the at least one fluid flow path; and selecting a second point at a second location of the at least one fluid flow path, wherein defining the guide curve comprises defining the guide curve from the first point to the second point such that the guide curve follows a direction of fluid flow through the at least one fluid flow path.

In some examples, defining the guide curve includes determining a centerline of at least a portion of the at least one fluid flow path. The centerline may be determined based on the lumen of the at least one fluid flow path. For example, defining the guide curve may comprise calculating a centerline path of the at least one fluid flow path, wherein the centerline path is bounded by the structure, and wherein the guide curve follows the centerline path.

In some examples, the process 1700 further includes spacing each of the plurality of planes from another one of the plurality of planes at regular intervals along the guide curve; rotating one or more of the plurality of planes about a point of intersection between the one or more of the plurality of planes and the guide curve, wherein the one or more of the plurality of planes are rotated by an angular increment along a first axis; and determining a surface area of each cross-section corresponding to each angular increment along the first axis.

In some examples, the process 1700 further includes rotating one or more of the plurality of planes about a point of intersection between the one or more of the plurality of planes and the guide curve, wherein the one or more of the plurality of planes are rotated by an angular increment along a second axis; and determining a surface area of each cross-section corresponding to each angular increment along the second axis.

In some examples, the process 1700 further includes defining a second plurality of planes, each of the second plurality of planes corresponding to a rotation of one of the one or more of the plurality of planes about a first axis perpendicular to the guide curve, each of the second plurality of planes intersecting the region to define at least some of the plurality of cross-sections of the region.

In some examples, the process 1700 further includes defining a third plurality of planes, each of the third plurality of planes corresponding to a rotation of one of the one or more of the plurality of planes about a second axis perpendicular to the guide curve and the first axis, each of the second plurality of planes intersecting the region to define at least some of the plurality of cross-sections of the region.

In some examples, the process 1700 further includes defining a fourth plurality of planes, each of the fourth plurality of planes corresponding to a rotation of one of the one or more of the plurality of planes, the second plurality of planes or the third plurality of planes about a third axis tangential to the guide curve, each of the second plurality of planes intersecting the region to define at least some of the plurality of cross-sections of the region.

In some examples, the process 1700 further includes dividing the plurality of planes into two or more subsets, wherein each of the two or more subsets include one or more planes, and wherein determining which one of the plurality of cross-sections has the smallest surface area comprises determining which one of the one or more planes in each subset has the smallest surface area.

In some examples, each subset consists of a selection of planes sharing an intersection point with the guide curve.

In some examples, the process 1700 further includes, based on the smallest surface area of each of the two or more subsets, profiling the smallest surface area along the guide curve to generate a smallest surface area profile.

In some examples, the process 1700 further includes, based on the smallest surface area profile, identifying a discrete stenosis or a tunnel stenosis.

In some examples, the plurality of images comprise a plurality of computed tomography (CT) scans of the structure.

In some examples, determining the region of the at least one fluid flow path further includes utilizing feature-recognition software to identify a portion of the structure that contains the region.

Using the systems and methods described above, a standardized method provides physicians and researchers the ability to determine a minimal neo-LVOT area for transcatheter mitral valve repair research and development as well as determining the appropriate sizing in the context of patient and procedure planning. Although the particular examples above relate to the mitral valve, a skilled artisan will appreciate that the principles, systems, and methods described above can be readily applied in connection with other types of surgical procedures and other areas of the anatomy. For example, in some embodiments, the valve may be a pulmonary branch valve, the tricuspid valve, etc. In other embodiments, the systems and methods described above may be used in the treatment of pulmonary artery stenosis, other valves, left atrial appendage (LAA) closure, stent grafts for aortic aneurysms, brain aneurysm devices, annular assessment (e.g., min/max area), etc. In certain embodiments, the systems and methods described may be used for airways, the treatment of airway conditions and the placement of artificial devices (e.g., stents, grafts, valves, drug-delivery systems, etc.) in airways, etc.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the disclosure, which is defined in the accompanying claims.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Further, one or more blocks/steps may be removed or added. For example, only portions of process 1700 illustrated with respect to FIG. 17 may be performed in certain embodiments, such as blocks 1702-1714 to determine which cross-section has a smallest surface area.

The methods disclosed herein comprise one or more steps or actions for achieving the described method. Various embodiments disclosed herein provide for the use of a computer system to perform certain or all method steps or actions. A skilled artisan will readily appreciate that such steps may be partly or entirely automated. Various embodiments disclosed herein comprise method steps that are partly or entirely performed by a user, or require the input of a user. A skilled artisan will readily appreciate that this user can be a medical professional, or a non-medical professional, such as a technician or engineer.

Various embodiments disclosed herein provide for the use of a computer system to perform certain features. A skilled artisan will readily appreciate that these embodiments may be implemented using numerous different types of computing devices, including both general-purpose and/or special-purpose computing system environments and configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general-purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special-purpose microprocessor such as a digital signal processor or a graphics processor. The microprocessor typically has conventional address lines, conventional data lines, and one or more conventional control lines.

Aspects and embodiments disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. A method for evaluating fluid flow, comprising:
generating a model of a structure based on a plurality of images of the structure, the structure comprising at least one fluid flow path;
determining a region of the at least one fluid flow path for flow analysis; and
performing the flow analysis, wherein performing the flow analysis comprises:
defining a guide curve along at least a portion of the at least one fluid flow path;
defining a first plurality of planes along the guide curve, each of the first plurality of planes orthogonal to the guide curve and intersecting the region to define at least some of a plurality of cross-sections of the region;
defining a second plurality of planes, each of the second plurality of planes corresponding to a rotation of one of the one or more of the first plurality of planes about a first axis perpendicular to the guide curve, each of the second plurality of planes intersecting the region to define at least some of the plurality of cross-sections of the region;
determining which one of the plurality of cross-sections has a smallest surface area; and
displaying a size of the smallest surface area.

2. The method of claim 1, wherein the model of the structure further comprises a virtual model of a prosthetic device, and further comprising selecting a revised virtual model of the prosthetic device based on a treatment plan to improve fluid flow in a second fluid flow path.

3. The method of claim 2, wherein:
the model of the structure comprises a model of at least a portion of a heart of a patient;
the region of the at least one fluid flow path for the flow analysis comprises a left ventricle outflow tract of at least the portion of the heart of the patient; and
the virtual model of the prosthetic device comprises a virtual model of a prosthetic mitral valve.

4. The method of claim 1, wherein defining the guide curve comprises:
selecting a first point at a first location of the at least one fluid flow path; and
selecting a second point at a second location of the at least one fluid flow path, wherein defining the guide curve comprises defining the guide curve from the first point to the second point such that the guide curve follows a direction of fluid flow through the at least one fluid flow path.

5. The method of claim 4, wherein:
the first point and the second point comprise points located at opposite ends of the at least one fluid flow path which are centered in the at least one fluid flow path; or
the first point comprises:
an arbitrary point located within the model of the structure,
a point indicated within the model of the structure,
an anatomical landmark within the model of the structure, or
a point at a center of the region of the at least one fluid flow path, and
the second point comprises a point near a fluid flow exit of the model of the structure.

6. The method of claim 1, wherein defining the guide curve comprises calculating a centerline path of the at least one fluid flow path, wherein the centerline path is bounded by the structure, and wherein the guide curve follows the centerline path.

7. The method of claim 1, wherein defining the guide curve comprises defining a straight line segment between a first point in the structure and a second point within a threshold of an exit of the at least one fluid flow path from the structure.

8. The method of claim 7, wherein the first point is one of a center or an apex of the structure.

9. The method of claim 7, wherein the structure is a left ventricle of a heart of a patient, and wherein the second point is one of a point near an aortic valve, a manually indicated point near the aortic valve, or a center of the aortic valve.

10. The method of claim 1, further comprising defining a third plurality of planes, each of the third plurality of planes corresponding to a rotation of one of the one or more of the first plurality of planes about a second axis perpendicular to the guide curve and the first axis, each of the third plurality of planes intersecting the region to define at least some of the plurality of cross-sections of the region.

11. The method of claim 10, further comprising defining a fourth plurality of planes, each of the fourth plurality of planes corresponding to a rotation of one of the one or more of the first plurality of planes, the second plurality of planes, or the third plurality of planes about a third axis tangential to the guide curve, each of the fourth plurality of planes intersecting the region to define at least some of the plurality of cross-sections of the region.

12. The method of claim 1, further comprising:
dividing a set of planes comprising the first plurality of planes and the second plurality of planes into two or more subsets, wherein each of the two or more subsets include one or more planes, and wherein determining which one of the plurality of cross-sections has the smallest surface area comprises determining which one of the one or more planes in each subset has the smallest surface area, wherein each subset consists of a selection of planes sharing an intersection point with the guide curve.

13. The method claim 12, further comprising, based on the smallest surface area of each of the two or more subsets, profiling the smallest surface area along the guide curve to generate a smallest surface area profile.

14. The method of claim 13, further comprising, based on the smallest surface area profile, identifying a discrete stenosis or a tunnel stenosis.

15. The method of claim 1, wherein the plurality of images comprise a plurality of computed tomography (CT) scans of the structure.

16. The method of claim 1, further comprising defining a fourth plurality of planes, each of the fourth plurality of planes corresponding to a rotation of one of the one or more of the first plurality of planes or the second plurality of planes about a third axis tangential to the guide curve, each of the fourth plurality of planes intersecting the region to define at least some of the plurality of cross-sections of the region.

17. An apparatus for evaluating fluid flow, comprising:
a memory; and
a processor communicatively coupled to the memory, the processor and the memory configured to:
generate a model of a structure based on a plurality of images of the structure, the structure comprising at least one fluid flow path;
determine a region of the at least one fluid flow path for flow analysis and perform the flow analysis, wherein performing the flow analysis comprises:
    defining a guide curve along at least a portion of the at least one fluid flow path;
    defining a first plurality of planes along the guide curve, each of the first plurality of planes orthogonal to the guide curve and intersecting the region to define at least some of a plurality of cross-sections of the region;
    defining a second plurality of planes, each of the second plurality of planes corresponding to a rotation of one of the one or more of the first plurality of planes about a first axis perpendicular to the guide curve, each of the second plurality of planes intersecting the region to define at least some of the plurality of cross-sections of the region;
    determining which one of the plurality of cross-sections has a smallest surface area; and
    displaying a size of the smallest surface area.

18. The apparatus of claim 17, wherein the model of the structure further comprises a virtual model of a prosthetic device, and wherein the processor and the memory are further configured to select a revised virtual model of the prosthetic device based on a treatment plan to improve fluid flow in a second fluid flow path.

19. The apparatus of claim 17, wherein defining the guide curve comprises:
    selecting a first point at a first location of the at least one fluid flow path; and
    selecting a second point at a second location of the at least one fluid flow path, wherein defining the guide curve comprises defining the guide curve from the first point to the second point such that the guide curve follows a direction of fluid flow through the at least one fluid flow path.

20. A non-transitory computer-readable storage medium that stores instructions that when executed by a processor of an apparatus cause the apparatus to perform a method for evaluating fluid flow, the method comprising:
    generating a model of a structure based on a plurality of images of the structure, the structure comprising at least one fluid flow path;
    determining a region of the at least one fluid flow path for flow analysis; and
    performing the flow analysis, wherein performing the flow analysis comprises:
        defining a guide curve along at least a portion of the at least one fluid flow path;
        defining a first plurality of planes along the guide curve, each of the first plurality of planes orthogonal to the guide curve and intersecting the region to define at least some of a plurality of cross-sections of the region;
        defining a second plurality of planes, each of the second plurality of planes corresponding to a rotation of one of the one or more of the first plurality of planes about a first axis perpendicular to the guide curve, each of the second plurality of planes intersecting the region to define at least some of the plurality of cross-sections of the region;
        determining which one of the plurality of cross-sections has a smallest surface area; and
        displaying a size of the smallest surface area.

\* \* \* \* \*